United States Patent
Guerra-Vela et al.

(10) Patent No.: US 6,799,464 B2
(45) Date of Patent: Oct. 5, 2004

(54) MACROSCOPIC MODEL OF SCANNING FORCE MICROSCOPE (75) Inventors: Claudio Guerra-Vela, Yabucoa, PR (US); Fredy R. Zypman, Englewood, NJ (US)

(73) Assignee: University of Puerto Rico, San Juan, PR (US)

( * ) Notice: Subject to any disclaimer, the term of this patent is extended or adjusted under 35 U.S.C. 154(b) by 103 days.

(21) Appl. No.: 09/800,805

(22) Filed: Mar. 7, 2001

(65) Prior Publication Data

US 2002/0152795 A1 Oct. 24, 2002

Related U.S. Application Data (60) Provisional application No. 60/187,706, filed on Mar. 7, 2000.

(51) Int. Cl.$^7$ ................................................. G01H 1/00
(52) U.S. Cl. ....................................................... 73/579
(58) Field of Search .......................... 73/1.89, 579, 105

(56) References Cited

U.S. PATENT DOCUMENTS

| | | | |
|---|---|---|---|
| 4,383,446 A | * | 5/1983 | Roeder et al. ................. 73/579 |
| 4,389,891 A | * | 6/1983 | Fournier ....................... 73/579 |
| 6,041,642 A | * | 3/2000 | Duncan ........................ 73/579 |
| 6,145,374 A | * | 11/2000 | Zypman Niechonski et al. ........................... 73/105 |

* cited by examiner

Primary Examiner—Robert Raevis
(74) Attorney, Agent, or Firm—Patent Law Offices of Heath W. Hoglund (57) ABSTRACT

A macroscopic version of the Scanning Force Microscope is described. It consists of a cantilever under the influence of external forces, which mimic the tip-sample interactions. The use of this piece of equipment is threefold. First, it serves as direct way to understand the parts and functions of the Scanning Force Microscope, and thus it is effectively used as an instructional tool. Second, due to its large size, it allows for simple measurements of applied forces and parameters that define the state of motion of the system. This information, in turn, serves to compare the interaction forces with the reconstructed ones, which cannot be done directly with the standard microscopic set up. Third, it provides a kinematics method to non-destructively measure elastic constants of materials, such as Young's and shear modules, with special application for brittle materials.

5 Claims, 5 Drawing Sheets

MACROSCOPIC MODEL OF SCANNING FORCE MICROSCOPE

CLAIM OF PRIORITY

Applicants claim the benefits of priority to U.S. patent applications 60/187,706 filed Mar. 7, 2000 and Ser. No. 09/545,570.

GOVERNMENT FUNDING

Aspects of the research related to this invention were supported by the National Science Foundation (grant no. DMR 9872689), Department of Energy (grant no. DE-FG02-98-ER-45729 and subcontract from UNM), National Cancer Institute (grant no. CA77796-01), and National Institutes of Health (grant no. SO6-GM08216).

FILED OF THE INVENTION

The invention relates generally to improving the measurement accuracy of a scanning force microscope (SFM) and more particularly to determining the resonant frequencies in a cantilever such as is used in an SFM.

BACKGROUND OF THE INVENTION

Figure 1:
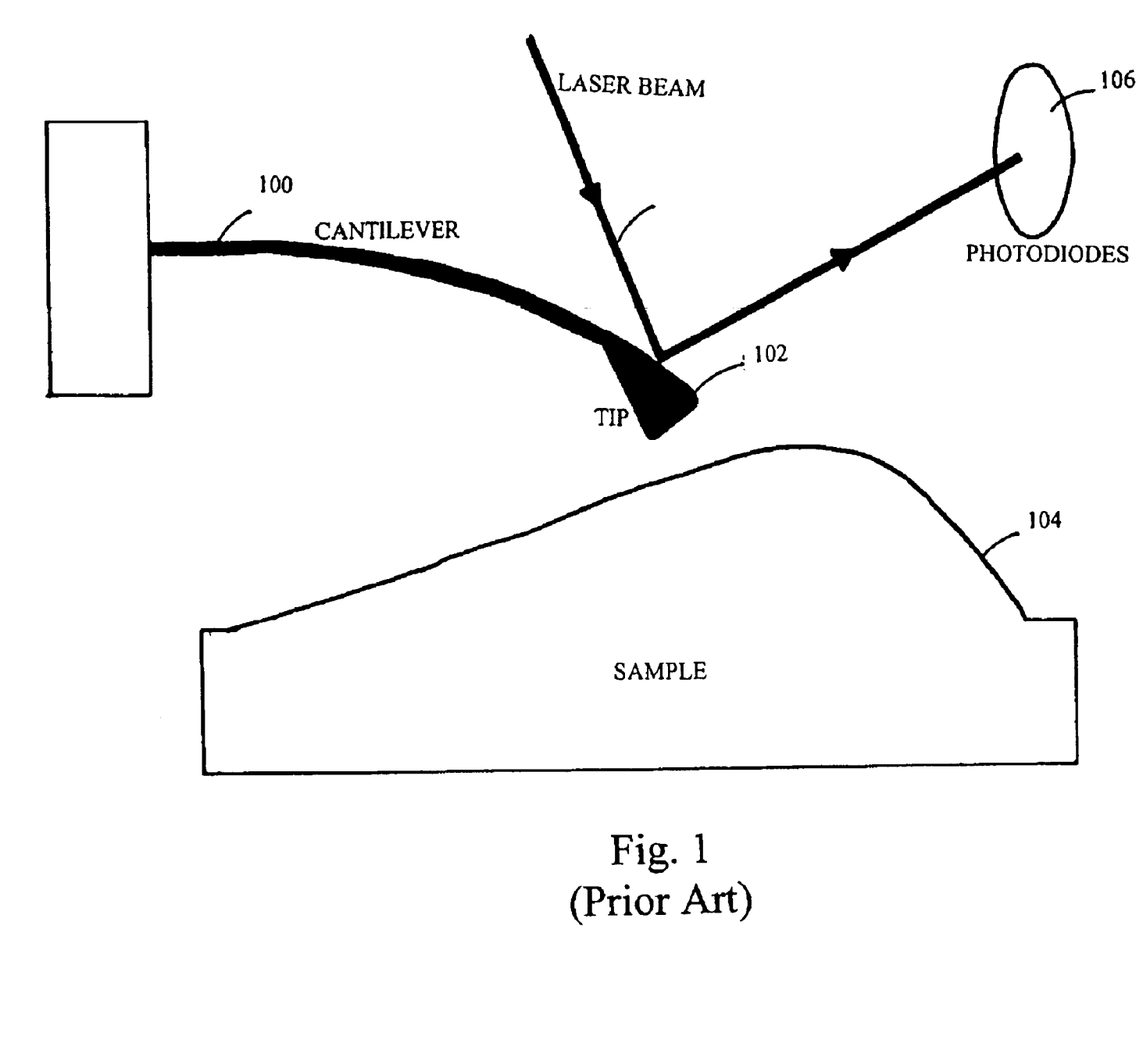
FIG. 1 shows a schematic diagram of one prior art SFM.

Scanning force microscopes are used in a broad range of fields. They can provide surface information at a very high resolution. A subset of SFMs utilize a flexible cantilever attached to a probe. FIG. 1 (Prior Art) shows one such SFM. The SFM includes a cantilever 100 and a tip 102, which are manufactured as a single piece of, typically, $SiN_3$ or C. The cantilever 100 measures about 100 $\mu$m in length, and the tip, made as regular tetrahedron, averages 10 $\mu$m in height. A transducer scans the tip 102 across the surface 104 under study and, meanwhile, the tip 102 interacts with the surface 104 via a variety of microscopic forces.

Tip 102 reflects a laser beam 106 to a group of photodiodes 108. The deflection or movement of the tip 102 is measured by detecting movement of the reflected laser beam 106.

The function of the cantilever 100 is to support the tip 102. The tip 102 thus plays the main role of the microscope. The cantilever 100, in turn, purports an ancillary purpose. However, any reconstruction algorithm must incorporate it as a pivotal element. A reconstruction algorithm converts experimental data into force information. More specifically, the sample rests on a vertically movable support. As the support moves, so do the tip-sample separation, and their interaction force. The objective of a "spectroscopic" SFM consists of retrieving the corresponding force-separation (that is force vs. tip-sample-separation) curve. On the other hand, experiments measure kinematic data. By means of the photodiode system and simple geometrical optics, the height of the tip 102 as a function of time, z(t), is recorded through photodiodes 108. Thus, any reconstruction algorithm reduces the kinematics into the force-separation curve. These two pieces of information are linked through the dynamics of the cantilever-tip system under the influence of the sought force.

Figure 2:
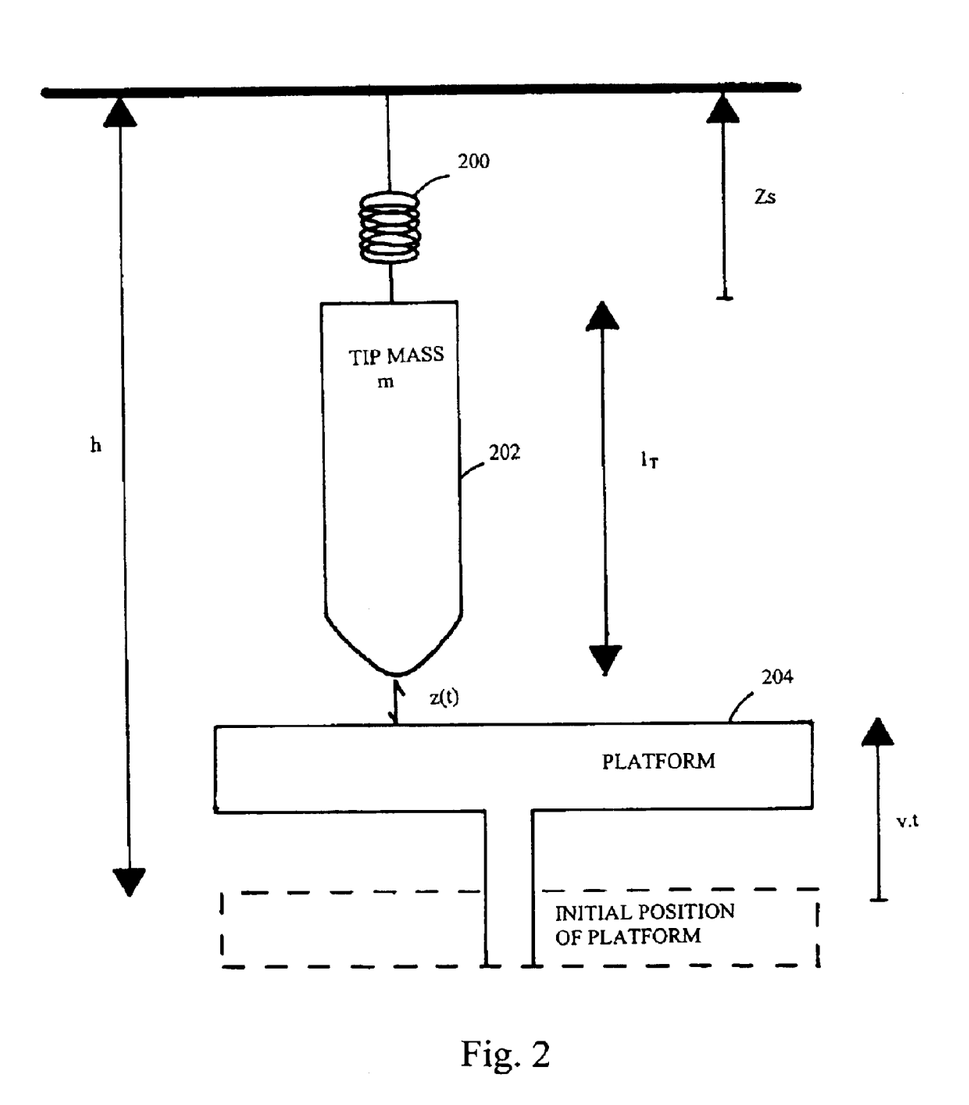
FIG. 2 shows a schematic diagram of one prior art model used evaluate the results from an SFM.

An earlier dynamics model that is still used extensively in analyzing data from an SFM is shown in FIG. 2. This model This model assumes that the elastic properties of the cantilever may be lumped into an effective spring constant, k, and the cantilever-tip inertia is considered through an effective mass, m. By this model spring 200 connects with the tip 202 that in turn interacts with a surface. As the sample-holder platform 204 moves upward at constant speed v, the tip-sample separation changes, and so does the tip-sample interaction. Within this framework and, by using Newton's second law, the interaction is $F(t)=md^2z(t)/dt^2+kz(t)$, where t represents the time elapsed since the platform started moving and, z(t), the tip's height is measured with the optical setup shown in FIG. 1.

While this model provides relatively good results, the accuracy of an SFM is limited by the underlying model. Improvements to this model are taught in U.S. Pat. No. 6,145,374 and in U.S. patent application Ser. No. 09/545,570, both to Zypman et al., which are incorporated herein by reference.

SUMMARY OF THE INVENTION

The interactions of a cantilever such as those used in a SFM are mathematically modeled as system having multiple resonant frequencies. Due to the small size of a cantilever actually used in an SFM, verification of any mathematical model are difficult, at best. To overcome that difficulty, a macroscopic cantilever is disclsoed along with effective methods of determing resonant frequencies of the cantilever system. According to one preferred aspect of the invention, the cantilever is on the order of at least one centimeter. Although the system is developed for determining the accuracy of mathematical models used in SFMs, preferred embodiments of the invetion may also be used to characterize the physical properties of materials such as Young Modulus. The methods may be used with britle materials such as ceramics or glass. In addition, non-linear elastic properties can be studied. This is of particular relevance in predicting the behavior of materials when performing as parts of mobile machinery.

According to one aspect of the invention, the accuracy of an SFM is improved based upon multiple resonance frequencies of a cantilever system. The cantilever is composed of a material having a known Young's modulus, E, and the the cross sectional area, A, length, L, and geometric moment of inertia, I, of the cantilever are determined. The vibrational modes of the cantilever system are calculated based upon the following equations:

$$\frac{1+\cos\xi_n \cdot \cosh\xi_n}{\sin\xi_n \cdot \cosh\xi_n - \cos\xi_n \cdot \sinh\xi_n}\xi_n^3 = \beta$$

$$n_n = \left(A^{\frac{1}{2}}V\right)\Big/(2pL^2)x_n^2$$

where:

$\beta = GL^3/EI$; and

G=slope of a force–distance curve

The SFM is electronically calibrated based upon these vibrational modes. According to a further aspect of the invention, the cantilever is excited by a piezoelectric crystal positioned near its base. Another piezoelectric crystal detects the vibrations at the free end of the cantilever. The excitation and detected signals are compared to determine the resonance frequencies of the system.

According to another aspect of the invention, the resonant frequencies of a cantilever system are determined. The cantilever has a length of at least one centimeter. An excitation is applied near the base of the cantilever and the displacement is measured through a transducer near the free end of the cantilever. The excitation signal is plotted against the detected signal. When a resonance frequency is generated, the plot will display a Lissajous figure.

According to a further aspect of the invention, the cantilever has a known spring constant, k. The slope of a force separation curve is then determined based upon the following equation:

$$\frac{1}{3}\frac{1+\cos\xi\cdot\cosh\xi}{\sin\xi\cdot\cosh\xi-\cos\xi\cdot\sinh\xi}\xi^3 = \frac{k}{\kappa}$$

According to another aspect of the invention, a measurement device is configured to detect the resonant frequencies of a cantilever. The measurement device includes a base, a cantilever, a pair of transducers and a display. The cantilever is attached to the base on one end and free, at the other end. The cantilever is at least on centimeter long. One of the transducers is positioned at the base and the other at the free end of the cantilever. A signal generator drives the transducer at the base at a single frequency that sweeps through a range. That excitation signal and the detected signal from the transducer at the free end are plotted on the display. According to a further aspect of the invention, the excitation is plotted against the detected signal so that resonant frequencies of the cantilever system generate a Lissajous figure. The resonat frequency is determined by a frequency counter connected with the signal generator.

DETAILED DESCRIPTION

Figure 3:
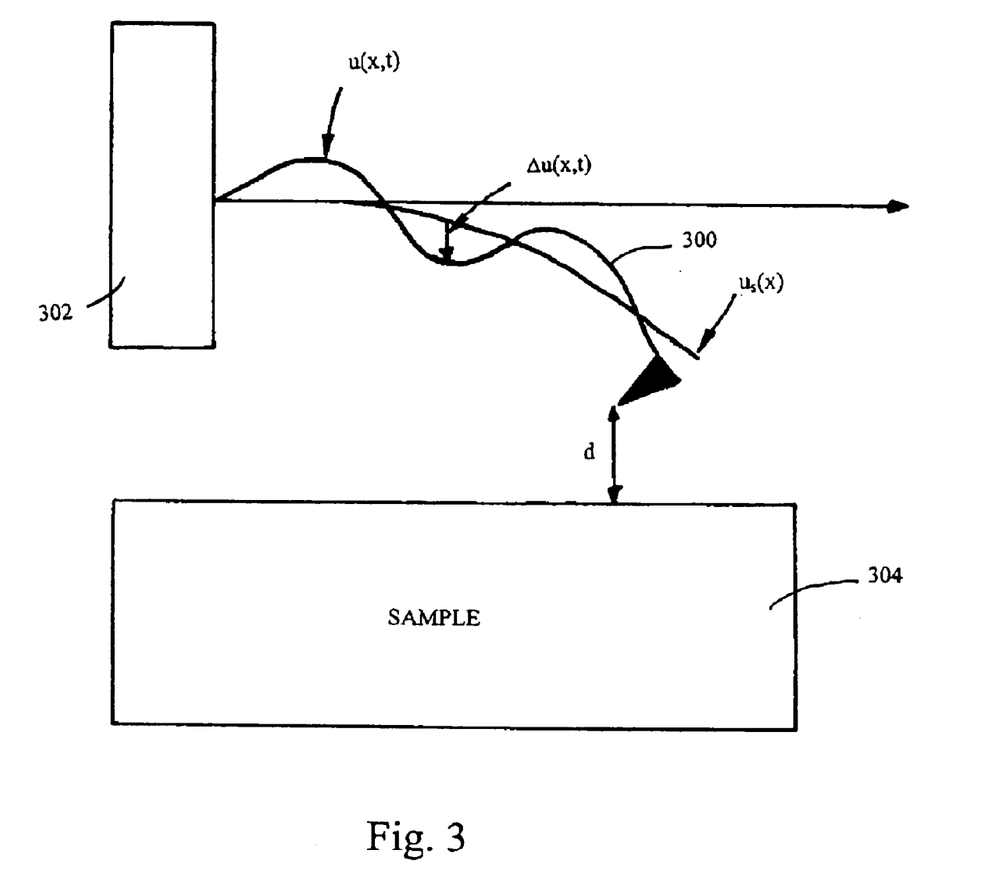
FIG. 3 shows a schematic diagram of an SFM including modes of oscillation that are not evaluated by the prior art model shown in FIG. 2.

The limitations of the model described above with reference to FIG. 2 requre an extension to the underlying mathematics supporting that model. Specifically, the cantilever of an SFM should be modeled as an extended object, capable of holding an infinite number of resonances. Concretely, FIG. 3, illustrates a model of a cantilever 300 in an SFM as a vibrating rod fixed at one end to a base 302, and interacting at the "free" end with a sample 304. In this extension, the cantilever is allowed to vibrate on a vertical plane.

For clarity, the following description is divided into a section detailing the mathematics underlying the model shown in FIG. 3, and a section detailing the physical validation of this model.

I. Improved Mathmatical Model

The cantilever is modeled as a beam governed by the following equation:

$$\frac{\partial^2}{\partial x^2}\left(EI\frac{\partial^2 u}{\partial x^2}\right) + \rho A\frac{\partial^2 u}{\partial t^2} = 0 \quad \text{Equation 1}$$

where u(x,t) is the deflection of the cantilever with respect to the horizontal at position x along the cantilever and at time t. E is the Young Modulus, I the (area) moment of inertia through middle axis perpendicular to the plane of motion, ρ is the density of the cantilever and A the cross-sectional area of the cantilever.

To simplify the analysis, the cross sectional area is held constant. In that case, the parameters do not vary with x. Thus, we can define:

$$V^2 \equiv \frac{EI}{\rho A^2} \quad \text{Equation 2}$$

Now we can rewrite Equation 1 as:

$$AV^2\frac{\partial^4 u}{\partial x^4} + \frac{\partial^2 u}{\partial t^2} = 0 \quad \text{Equation 3}$$

In order to solve Equation 3, we need to set appropriate boundary conditions (BC). These conditions will also introduce the tip-sample interaction force that is to be measured. At the fix end of the cantilever (x=0) we impose no deflection, thus:

$$u(x=0,t) \equiv 0 \quad \text{(Equation 3a)}$$

Also, since the lever is not free to rotate about that point:

$$\frac{\partial u}{\partial x}(x=0,t) \equiv 0 \quad \text{(Equation 3b)}$$

At the free end, x=L, the cantilever experiences no torque if we consider vertical interaction forces:

$$\frac{\partial^2 u}{\partial x^2}(x=L,t) \equiv 0 \quad \text{(Equation 3c)}$$

Finally, at the free end, the internal force on that layer of cantilever must equal the external force, so that the boundary condition is:

$$-EI\frac{\partial^3}{\partial x^3}u(x=L,t) = F[u(x=L,t)] \quad \text{(Equation 3d)}$$

A. Static Solution

Typically, the scientific community has used a solution to the previous problem for which the interaction force F is slowly varying with time. This renders a quasistatic solution corresponding to the patching of a series of solutions for which F=Fs, with Fs a constant force.

In this static case, Equation 3 reduces to:

$$\frac{\partial^4 u_S(x,t)}{\partial x^4} = 0 \quad \text{(Equation 4)}$$

where we have added the subindex S for u, to indicate a static solution. This equation, in conjunction with the four BC provides a unique solution:

$$u_S(x) = \frac{(3F_S L)x^2 - (F_S)x^3}{6EI} \quad \text{(Equation 5)}$$

If the SFM monitors the deflection of one point of the cantilever, say x=L (it can be easily extended to any point), then the measured deflection, $z_s$, would be describe as follows:

$$z_S(t) = \frac{F_S(t)L^3}{3EI} \quad \text{(Equation 6)}$$

As the force varies slowly with time, so does the deflection. This time dependence is explicit in Equation 6 to stress that measurements are made in time steps. This solution corresponds to a one-degree-of-freedom, simple-harmonic-oscillator (SHO) approximation of the cantilever with spring constant $3EI/L^3$. As an approximation, it has several limitations. In particular, it will fail when the tip-sample interaction force does not vary slowly. Under those circumstances, it may be possible to excite vibrational modes on the cantilever and, consequently, a one-degree of freedom model will not be enough to determine the state of the system. In the quasistatic regime, on the other hand, one degree of freedom is enough because if z(t) is measured, then Equations 5 and 6 can be used to compute the entire shape of the cantilever.

B. Generalizing the SHO Solution

In order for the SFM to be of use in fast imaging, where a force-distance curve must be obtained for each pixel and as quickly as possible, for example in the study of biomolecular motion, the quasistatic solution must be revisited because it does not yield accurate results.

With that in mind, we now generalize the previous problem by allowing for the cantilever to sense, not only a constant force, but also a gradient of the force-distance curve as the tip moves away or towards the surface. This will enrich the solution for the deflection u(x,t), by allowing the possibility of vibrations superimposed on the SHO solution.

Therefore, we write the force as:

$$F = F_s + G[u(L,t) - u_s(L)] \quad \text{(Equation 7)}$$

In writing Equation 7, we assumed, as in the BC, that the force on the cantilever is applied on the tip at x=L. Here Fs is the average force the tip senses at one location above the sample, and G is the derivative of the force-distance curve at that same position.

We write the solution u(x,t) to Equation 3 as the sum of the static solution and a superposition of normal modes:

$$u(x,t) = u_S(x) + \sum_n f_n(x)\cos(\omega_n t + \varphi_n) \quad \text{(Equation 8)}$$

where $f_n(x)$ are the normal modes, $\omega_n$ is the angular frequency corresponding to $f_n(x)$, and $\phi_n$ is the phase of mode n.

Substituting Equation 8 into Equation 3 and noticing that $f_n(x)$ are linearly independent, we obtain:

$$\frac{d^4 f_n(x)}{dx^4} - \frac{\omega_n^2}{AV^2} f_n(x) = 0 \quad \text{(Equation 9)}$$

with solutions:

$$f_n(x) = f_n^1 \cos kx + f_n^2 \sin kx + f_n^3 \cosh kx + f_n^4 \sinh kx \quad \text{(Equation 10)}$$

where $f_n^1, f_n^2, f_n^3, f_n^4$ are constants and $k^4 = \omega_n^2/(AV^2)$. Next we apply the BC of Equations 3a, 3b, 3c and 3d and end up with BC for each individual mode $f_n(x)$ $$f_n^1 + f_n^3 = 0 \quad \text{(Equation 11a)}$$

$$f_n^2 + f_n^4 = 0 \quad \text{(Equation 11b)}$$

$$-f_n^1 \cos kL - f_n^2 \sin kL + f_n^3 \cosh kL + f_n^4 \sinh kL = 0 \quad \text{(Equation 11c)}$$

$$k^3(-f_n^1 \sin kL + f_n^2 \cos kL - f_n^3 \sinh kL - f_n^4 \cosh kL) = \gamma(f_n^1 \cos kL + f_n^2 \sin kL + f_n^3 \cosh kL + f_n^4 \sinh kL) \quad \text{(Equation 11d)}$$

where $\gamma = G/EI$.

In order for the system of equations 11a, 11b, 11c and 11d not to have trivially null solutions, we must require that the determinant of the system be zero. Thus $$k^3(1+\cos kL \cdot \cosh kL) = \gamma(\sin kL \cdot \cosh kL - \cos kL \cdot \sinh kL) \quad \text{(Equation 12)}$$

And with the definitions $\beta = \gamma L^3$, $\zeta_n = k_n L$, one obtains a transcendental equation for the frequencies $\phi_n$ for a given reduced force-separation slope, $\beta$, $$\frac{1 + \cos\xi_n \cdot \cosh\xi_n}{\sin\xi_n \cdot \cosh\xi_n - \cos\xi_n \cdot \sinh\xi_n} \xi_n^3 = \beta \quad \text{(Equation 13)}$$

Figure 4:
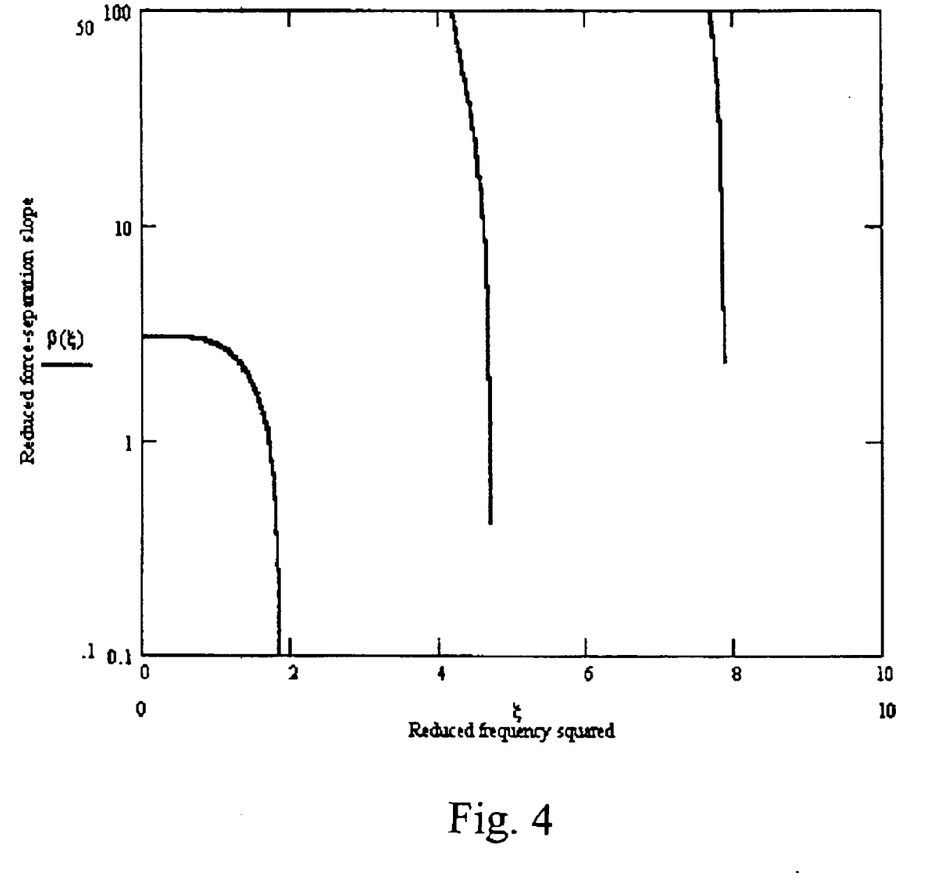
FIG. 4 shows a plot of the reduced force-separation slope, β, plotted as a function of reduced frequency squared, ξ.

From this equation, the frequencies of the normal modes are calculated from the expression $n_n = (A^{1/2} V)/(2pL^2) x_n^2$. The curve $\beta(\zeta)$ is shown in FIG. 4. There, the first three branches, corresponding to the lower three eigenfrequencies of the system, are drawn. For a given force-separation slope, $\beta$, corresponding to a horizontal line in the graph, there are three corresponding intersections and thus three frequencies.

This illustrates a number of important features. For one, the first, or lowest, eigenfrequency is very sensitive to changes in $\beta$. Higher-frequency branches are not as sensitive. In fact, they correspond to almost constant frequencies, independent of $\beta$. Next, for $\beta > 3$ ($\beta = 3$ corresponds to the snap-to-contact point where the slope of the force-separation curve equals the spring constant, k), the real frequency coming from the first branch is lost. The "frequency" becomes purely imaginary, corresponding to a damping of the nodeless mode beyond the snap-to-contact point. In addition, the lowest frequency now is given by the intersection of $\beta$ = constant with the second branch of the curve. This means that the cantilever becomes stiffer. If $\beta$ is seen as an order parameter, and stiffness the property under study, one can say that at the snap-to-contact point there is a second order phase transition.

Equation 13 shows one of the primary results of this section. For convenience we can define the following additional notation: k=G and $\kappa = 3EI/L^3$. Where, as before, k (and G) is the slope of the force-separation curve at a given point of the curve. In addition:

$$\frac{1}{3} \frac{1 + \cos\xi \cdot \cosh\xi}{\sin\xi \cdot \cosh\xi - \cos\xi \cdot \sinh\xi} \xi^3 = \frac{k}{\kappa} \quad \text{(Equation 14)}$$

from Equation 6, $\kappa$ is the nominal, or manufacturer, "spring constant" of the cantilever-tip system.

Therefore, for a given cantilever-tip, $\kappa$ is known. The parameter k is in the real setup unknown (and the desired measured quantity). If the frequency spectrum is measured, the right-hand side of Equation 14 can be evaluated and thus k can be obtained.

II. Physical Validation

SFMs are by design very small. Typically, the cantilever extends on the order of 100 $\mu$m. Due to this small size, it is difficult to measure the accuracty of the above-detailed mathmatical model. To overcome this difficulty, a macroscopic cantilever on the order of at least one centimeter is used. Specifically, in the embodiment shown in FIG. 5, the cantilever 500 measures 25 cm. Although this is significantly larger than the typical cantilevers that are used in SFMs, the physics is the same for both systems; both are governed by classical mechanics. Forces of quantum mechanical origin do appear between the SFM tip and a sample. However, the origin of the force does not affect the application of our algorithm. Moreover, once a force is applied, regardless of its origin, the behavior of the macroscopic cantilever as with a SFM cantilever evolves in accordance with classical pyhsicals. Thus a cm-size cantilever is a good realization of the system under consideration.

Figure 5:
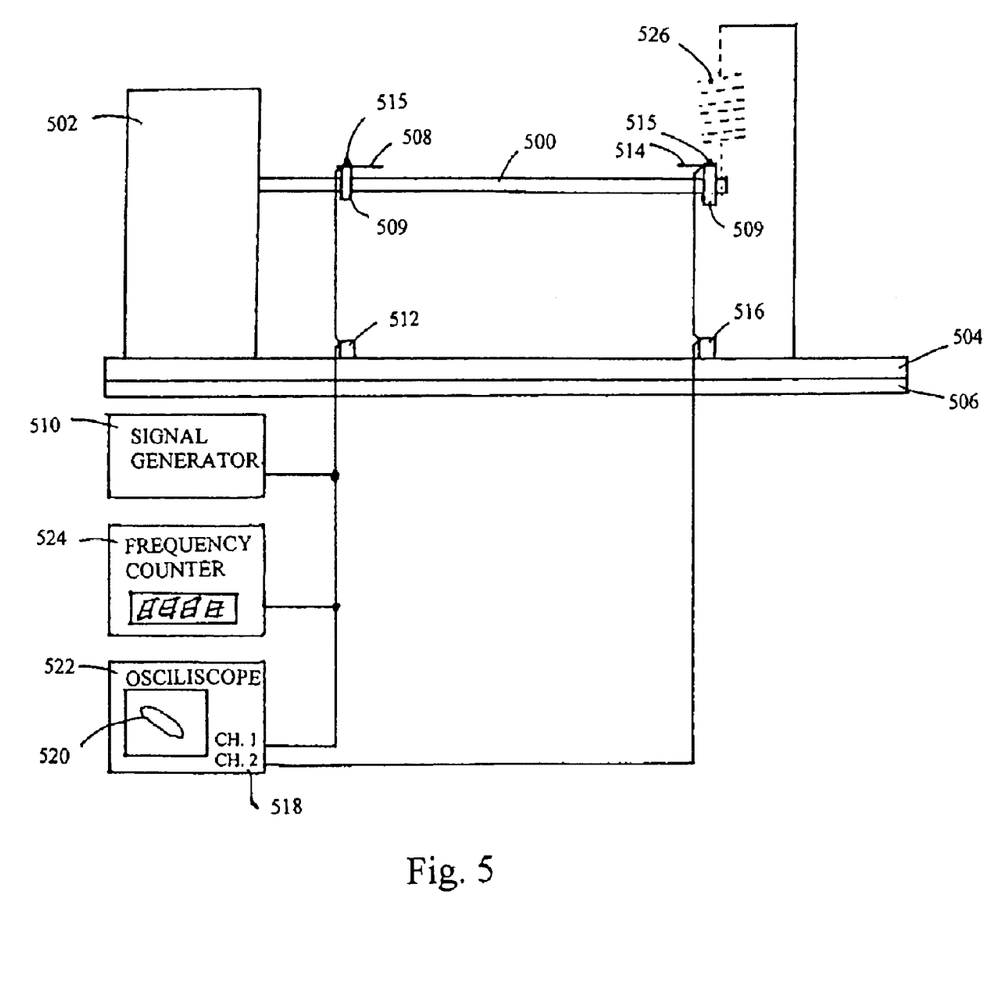
FIG. 5 shows a schematic diagram of one preferred system configured to determine the resonance frequencies in a macroscopic cantilever.

Turning to FIG. 5 one preferred system and related methods of detecting the resonant frequencies in a cantilever system are described. The system includes a 25 cm-long aluminum rod, or cantilever 500, that is attached to a heavy aluminum block 502. The block 502 is in turn attached to an aluminum horizontal slab base 504, where electrical connections to the cantilever 500 are made. For mechanical isolation and to improve the signal-to-noise ratio, the base 504 lies on a cushion foam pad 506.

A piezoelectric crystal 508 excites vibrations in the cantilever 500. The piezoelectric crystal is positioned near the base. An audio-frequency signal generator 510 drives the piezoelectric crystal 508. Electrical connection between the generator 510 and the piezoelectric crystal 508 are made through a connection block 512 on base 504.

A second piezoelectric crystal 514 is attached to the free extreme of the cantilever 500. Any electrical signal from the piezoelectric crystal 514 is fed through a connection block 514 on base 504 to an oscilliscope 518. The oscilliscope 518 provides dual channels. One is used to receive the excitation signal from signal generator 510 and the other is used to receive the detected signal from piezoelectric cyrstal 514. These two signals are plotted against each other so that any resonance frequencies that are propigated from piezoelectric crystal 508 to piezoelectric crystal 514 will generate a Lissajous FIG. 520 on the display 522 of the oscilliscope 518. In addition, the excitation signal from the signal generator 510 is also fed to a frequency counter 524.

To reduce noise, piezoelectric crystals 508 and 514 are buffered by teflon rings 509. Screws 515 pass through the associated transducers (i.e. piezoelectric crystals 508 and 514) and through the teflon rings 515 to engage treaded holes in cantilever 500.

One preferred method of determining the resonant frequencies of cantilever 500 is performed by scanning the signal generator 510 from low to high frequencies. If the excitation frequency is not a resonance, no mode is propagated away form the piezoelectric crystal 508 to piezoelectric crystal 514. When the signal generator 510 hits a resonance, a normal, extended, mode is excited which can be measured by the second piezoelectric crystal 514. To detect that resonance, the signal from the first piezo is connected to the vertical channel of oscilliscope 518, and the signal from the second piezo is connected to the horizontal channel of oscilliscope 518. The oscilloscope is set to operate in x-y mode so that an ellipse is detected when the cantilever is in resonance. When such an ellipse is detected, the resonance frequency may be determined from the frequency counter 524.

These detected values are compared to the theoretical values calculated in accordance with Equation 14, above. When the cantilever is not loaded, k=0 in Equation 14. Thus, the predicted frequency values are related to $\zeta_n$, and can be rewritten as:

$$v_n = \frac{1}{2\pi} \sqrt{\frac{\kappa}{3m}} \xi_n^2 \quad \text{(Equation 15)}$$

where n=1,2,3, identify the corresponding normal modes, and m=$\rho$Al is the total mass of the cantilever. For the embodiment shown in FIG. 5, m =(9.98±0.05) g, and $\kappa$=(624±9)N/m. Thus, the expected resonance frequencies may be calculated and are listed in the following table:

TABLE I

| n | $\xi^2$ | frequency (Hz) (expected) |
|---|---|---|
| 1 | 3.52 | 81.0 |
| 2 | 22.0 | 506 |
| 3 | 61.7 | 1.42 × 10³ |
| 4 | 121 | 2.78 × 10³ |
| 5 | 200 | 4.60 × 10³ |
| 6 | 299 | 6.88 × 10³ |
| 7 | 417 | 9.59 × 10³ |

A comparison between the detected resonce frequencies yields close agreement with the expected values. The detected resonance frequencies can then be used to determine an effective cantilever length and an effective spring constant, $\kappa_{eff}$. For example, for measured resonance frequenies of 62, 437, 1.24×10³, 2.38×10³, 4.19×10³, 6.24×10³, and 8.43×10³, the effective length is approximately 22 cm and the effective spring constant is approximately 527 N/m.

The accuracy of the above-described mathmatical algoritm can also be verified by appling a known force to the free end of the cantilever 500. For the embodiment of FIG. 5, a spring having a known spring constant is used to apply that force. (The spring 526 is shown in ghost lines in FIG. 5). The value of that force may be easily determined by |F|=(spring constant)×(deflection). Thus, the derivative of F with respect to the deflection is the spring constant which then must be equated with k in Equation 14. On the other hand the aluminum rod with dimensions L=(20.5±0.1)cm and r=2.38 mm (with negligible uncertainty) has a nominal constant k=(624±9)N/m. Thus for each external spring, the right hand side of Equation 14 is known and the resonant frequencies can be found.

A comparison between the expected and actual frequency shifts yields close agreement. For the embodiment of FIG. 5, the measured results are listed in the following table:

TABLE II

| k | k/$\kappa$ | f (Hz) | $\xi$ |
|---|---|---|---|
| 0 | 0 | 62 ± 1 | 1.88 |
| 267 | 0.507 ± 0.008 | 42 ± 1 | 1.51 |
| 308 | 0.544 ± 0.009 | 39 ± 1 | 1.46 |
| 364 | 0.691 ± 0.011 | 35 ± 1 | 1.39 |

The forgoing methods provide an effective way of verifying the accuracy of the mathematical models described above. These models, in turn, for improved accuracy in measuremnts made using an SFM. Although the methods have been applied as directed to verifying the mathematical models described above, these methods may be used in a number of other benefical applications. Specifially, the methods may be used to characterize the elastic properties of a material having unknown properties. In this case, the subject material is made in the shape of a cantilever and its resonance frequencies are determined in accordance with the methods described above. From Equations 2 and 9 the Young Modulus can be determined. This characterization technique is especially applicable to brittle materials such as ceramics or glass. In addition, non-linear elastic properties can be studied. This is of particular relevance in predicting the behavior of when performing as parts of mobile machinery.

Although the invention has been described with reference to specific embodiments, those skilled in the art will appreciate that many modifications may be made without departing from the teachings of the invention. The following claims intend to encompass all such modifications.

We claim:

1. A method of determining the resonant frequencies of a cantilever comprising the steps of:

fixedly attaching a cantilever to a base, wherein a distal end of the cantilever remains free, and wherein, the cantilever has a known spring contestant k;

exciting the cantilever proximate the base, wherein the excitation occurs through a range of frequencies;

measuring any displacement in the distal end of the cantilever simultaneous to the step of exciting the cantilever;

detecting a plurality of resonance frequencies by comparing the measured displacement in the distal end of the cantilever to the excitation; and determining a slope force separation curve, k, based upon the following equation:

$$\frac{1}{3} \frac{1 + \cos\xi \cdot \cosh\xi}{\sin\xi \cdot \cosh\xi - \cos\xi \cdot \sinh\xi} \xi^3 = \frac{k}{\kappa}.$$

2. The method of claim where 1, wherein the step of exciting the cantilever comprises attaching a first piezo-electric crystal to the cantilever proximate the base and electrically exciting the first piezo-electric crystal.

3. The method of claim 2, wherein the step of measuring any displacement in the distal end of the cantilever comprises attaching a second piezoelectric crystal to the distal end of the cantilever rind measuring an electric signal generated by the second piezo-electric crystal.

4. The method of claim 3, wherein the step of detecting the plurality of resonance frequencies comprises plotting the electrical excitation of the first piezoelectric crystal against the measured signal generated by the second piezoelectric crystal.

5. The method of claim 3, wherein the step of attaching a second piezoelectric crystal to the distal end of the cantilever further comprises positioning a buffer between the cantilever and the piezoelectric crystal.

* * * * *